United States Patent [19]
Fascetti et al.

[11] Patent Number: 5,874,295
[45] Date of Patent: Feb. 23, 1999

[54] ARTHROBACTER SP. AND ITS USE FOR THE DESULFURATION OF FOSSIL FUELS

[75] Inventors: Eugenio Fascetti, Rome; Ezio D'Addario, Monterotondo; Roberto Gianna, Rome; Pasquale Sacceddu, Monterotondo; Luca Serbolisca, Milan; Andrea Robertiello, Rome, all of Italy

[73] Assignee: Eniricerche S.p.A., Milan, Italy

[21] Appl. No.: 807,368

[22] Filed: Feb. 27, 1997

[30] Foreign Application Priority Data

Mar. 9, 1996 [IT] Italy .................................. MI96A0477

[51] Int. Cl.⁶ ..................................................... C10G 32/00
[52] U.S. Cl. ........................ 435/282; 435/252.1; 435/830
[58] Field of Search ................................ 435/252.1, 282, 435/830

[56] References Cited

U.S. PATENT DOCUMENTS 5,496,723  3/1996  Murzakov et al. .................. 435/252.1
5,516,677  5/1996  Kilbane, II .............................. 435/195

*Primary Examiner*—David A. Redding
*Attorney, Agent, or Firm*—Oblon, Spivak, McClelland, Maier & Neustadt, P.C.

[57] ABSTRACT

The invention relates to a strain of Arthrobacter sp. CBS 208.96 capable of selectively effecting the opening of the C-S bond of sulfurated organic molecules present in carbonaceous materials and its use in a process for the selective removal of organic sulfur from fossil fuels contained therein.

9 Claims, 5 Drawing Sheets

ARTHROBACTER SP. AND ITS USE FOR THE DESULFURATION OF FOSSIL FUELS

The present invention relates to a strain of Arthrobacter sp. capable of selectively opening the C-S bond of sulfurated organic molecules present in carbonaceous materials and its use in a process for the selective removal of organic sulfur from fossil fuels contained therein.

Fossil fuels refer to crude oil and its fractions, petroleum distillates, residues of petroleum distillation, etc.

It is now well-known that the use of fossil fuels with a high content of sulfur is the main cause of the phenomenum of acid rain which creates environmental problems at times of an extremely serious nature. For this reason the legislation already existing or about to be issued in North America, Europe and Japan tends to limit the consumption of fossil fuels with a high content of sulfur as much as possible. For example, in the United States, the Environmental Protection Agency (EPA) requested, as of 1994, that the percentage of sulfur in diesel fuel be reduced from 0.27% to values of less than 0.05%.

In addition, also the EEC regulation requires a lowering of the sulfur content in conformity with what has already been established in the U.S.A.. Much more restrictive limits are in force in Scandinavian countries (Sweden and Finland).

It is evident that the supplies of fossil fuels capable of satisfying the new regulations will be rapidly used up and it will be necessary to find efficient and economical technologies for removing the sulfur from fossil fuels before their final use.

Crude oil, as also fractions of petroleum and various petroleum products, in fact, often contain high quantities of sulfur. For example, in crude oil sulfur is present in percentages varying from 0.025 to 5% and in heavy fractions it also reaches 10%. In crude oil sulfur is present in small traces in the form of elemental sulfur, sulfates and hydrogen sulfide but it is mainly incorporated in the organic matrix in the form of sulfides, thiols, thiophenes, benzo and dibenzothiophenes variously substituted. In particular, in some crude products, such as the petroleum of Texas, about 70% of sulfur is present in the form of dibenzothiophene (DBT) and its alkyl derivatives.

Whereas compounds of inorganic sulfur can be easily removed by physico-chemical treatment, the removal of organic sulfur is a big problem.

The conventional processes of industrial desulfuration of petroleum, adopted at present, use the hydrodesulfuration technique (HDS) which consists in the reduction of the C-S bonds to hydrogen sulfide ($H_2S$) by the reaction of hydrogen with the fuel at high pressures and temperatures and in the presence of metal catalysts. Whereas the HDS process does not seem to create problems of a technical nature for the desulfuration of so-called labile compounds, further separation seems hindered, viceversa, by the refractariness to the hydrodesulfuration of organic molecules with an aromatic structure containing heteroatoms (refractory molecules). These refractory molecules normally require operating conditions of hydrodesulfuration processes (Deep HDS) that are so severe as to cause degradation also of quite a considerable quantity of hydrocarbons. In addition, the high concentration of heavy metals in the petroleum limits the use of the hydrodesulfuration process as heavy metals, as is known, poison the catalysts used in this process. As both the concentration of sulfurated compounds and that of heavy metals increase considerably during refining, the problem of removing organic sulfur from residual fuel oil is even more difficult to solve. For this reason these known processes do not represent an acceptable solution to the problem.

This explains why in the last fifty years intense studies have been carried out on the possibility of using microorganisms for removing, in the precombustion phase, organic sulfurated compounds present in fuels.

Numerous processes have been described in literature for removing organic sulfur which are based on the use of both anaerobic sulfate-reducer microorganisms which cause the production of $H_2S$, and aerobic oxidating microorganisms which cause the formation of inorganic forms soluble in water, such as sulfate and sulfuric acid. Most aerobic microorganisms degrade dibenzothiophene (DBT), used as model molecule, using the metabolic pathway described by Kodama (Agr. Biol. Chem., 34, 1320 (1970)).

According to this metabolism, the DBT is demolished starting from one of the benzene rings to give derivatives of benzothiophene and therefore molecules still containing sulfur. Although the removal of this compound is technically possible by extraction with water owing to its hydrosolubility, a desulfuration process which involves treatment of petroleum with these microorganisms and the subsequent removal of the hydrosoluble products containing sulfur would be too costly in consideration of the energy power losses due to the removal of the carbonaceous structure of the DBT and DBT-like compounds.

A similar result would be obtained if the metabolism were induced to proceed to the complete degradation of the starting sulfurated molecule.

Figure 1:
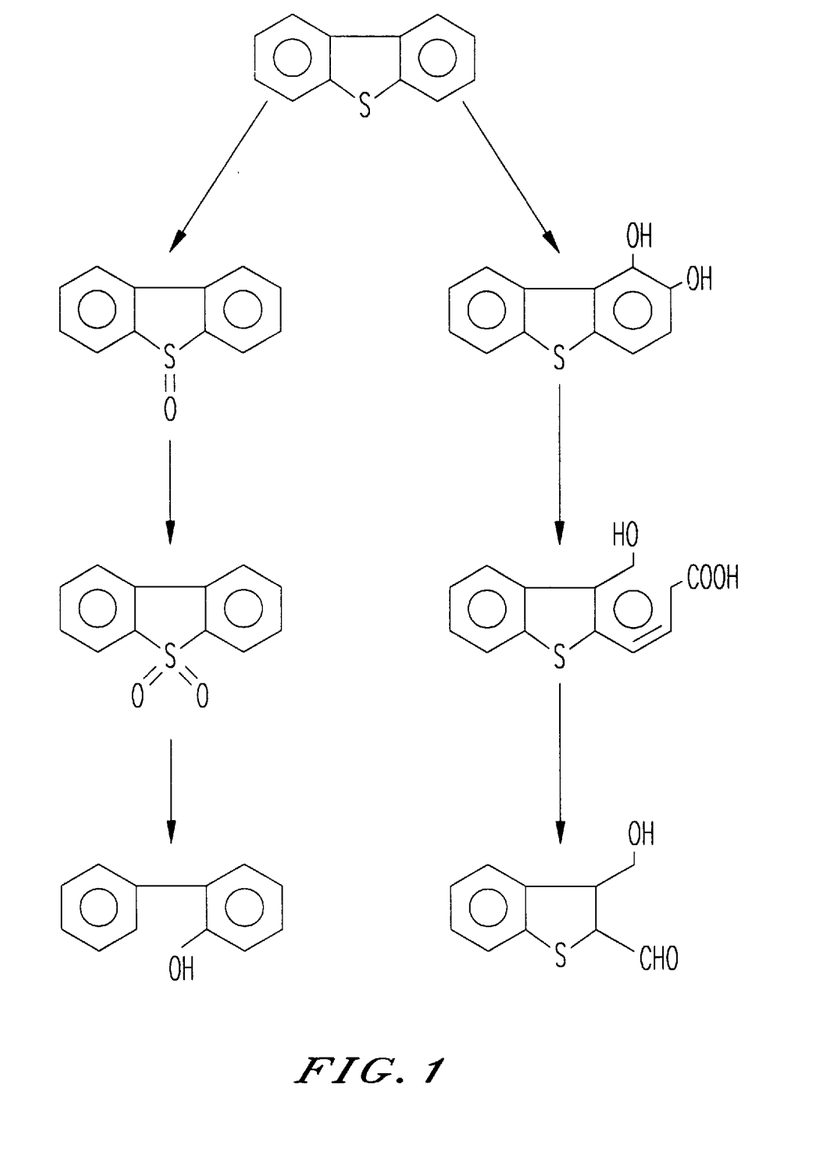
FIG. 1: Degradative pathway of dibenzothiophene according to the 4-S way.

Microorganisms have recently been described in the art, which are capable of removing sulfur from dibenzothiophene by means of a metabolic pathway (also called 4S), sulfoxide-sulfone-sulfonate-sulfate, which proves to be specific for desulfuration as it removes the sulfur from DBT leaving the carbonaceous structure intact and accumulating 2-hydroxybiphenyl (FIG. 1).

For example Kilbane et al. have described the isolation of a strain of *Rhodococcus rhodochrous* capable of removing sulfur from dibenzothiophene using the metabolic "4S" pathway with the production of 2-hydroxybiphenyl (U.S. Pat. No. 5.358.870, U.S. Pat. No. 5.132.219, PCT/U.S. Pat. No. 92/01868, EP 0 445 896 A2).

Operating with this microorganism however, it is necessary to use surfactants to maintain the petroleum product in close contact with the microbic suspension. The use of these agents, as well as considerably increasing the overall cost of the process, creates great difficulties in the subsequent separation step of the phase.

The processes using this microorganism are typically carried out by means of:

1. fermentation of the microorganism in the presence of carbon sources and other nutrients;
2. separation of the biomass from the culture medium;
3. use of the biomass as catalyst of the desulfuration reaction which is carried out in completely stirred reactors and in the presence of large quantities of water (at least 1:1 by volume of the oil);
4. separation of the phases which form part of the reaction with suitable equipment;
5. recycling of the paste phase, consisting of the catalyst, to the desulfuration reactor after flushing and reintegration of a quantity to keep the catalytic performance constant;
6. filtration of the aqueous phase to maximize the recovery of the catalyst;
7. addition of calcium salts (live or hydrated lime) or ammonium salts (hydroxide ion) to the aqueous stream at the outlet, to be able to proceed with the removal of the sulfate obtained by the oxidation of the sulfur; (the use of the ammonium ion foresees the concentration of the solution in order to be able to proceed with the separation of the ammonium sulfate owing to the high solubility of this salt); and 8. removal of the water from the desulfurated oil phase with the use of high efficiency separators (electrostatic separators).

These processes of the known art have the following main disadvantages:
- use of large quantities of water to favour the performance of the biocatalyst which carries out its activity in a prevalently aqueous environment;
- use of surfactants with a high concentration in the reaction mixture (0.5%) to favour the dispersion of the oil phase in the aqueous phase and facilitate the convey phenomena of the substrate towards the biocatalyst;
- use of high efficiency equipment for the separation of the phases at the outlet of the bioreactor to break up the emulsions generated by the use of the surfactant;
- high disposal costs in the landfill of the calcium sulfate produced or the necessity of having to commercially dispose of the ammonium sulfate alternatively produced;
- substantial recycling of the sulfate to the desulfuration reactor (the solubility of calcium sulfate at 20° C. is equal to 0.2/100 g, whereas ammonium sulfate is highly soluble) with consequent possible product inhibition.

Figure 2:
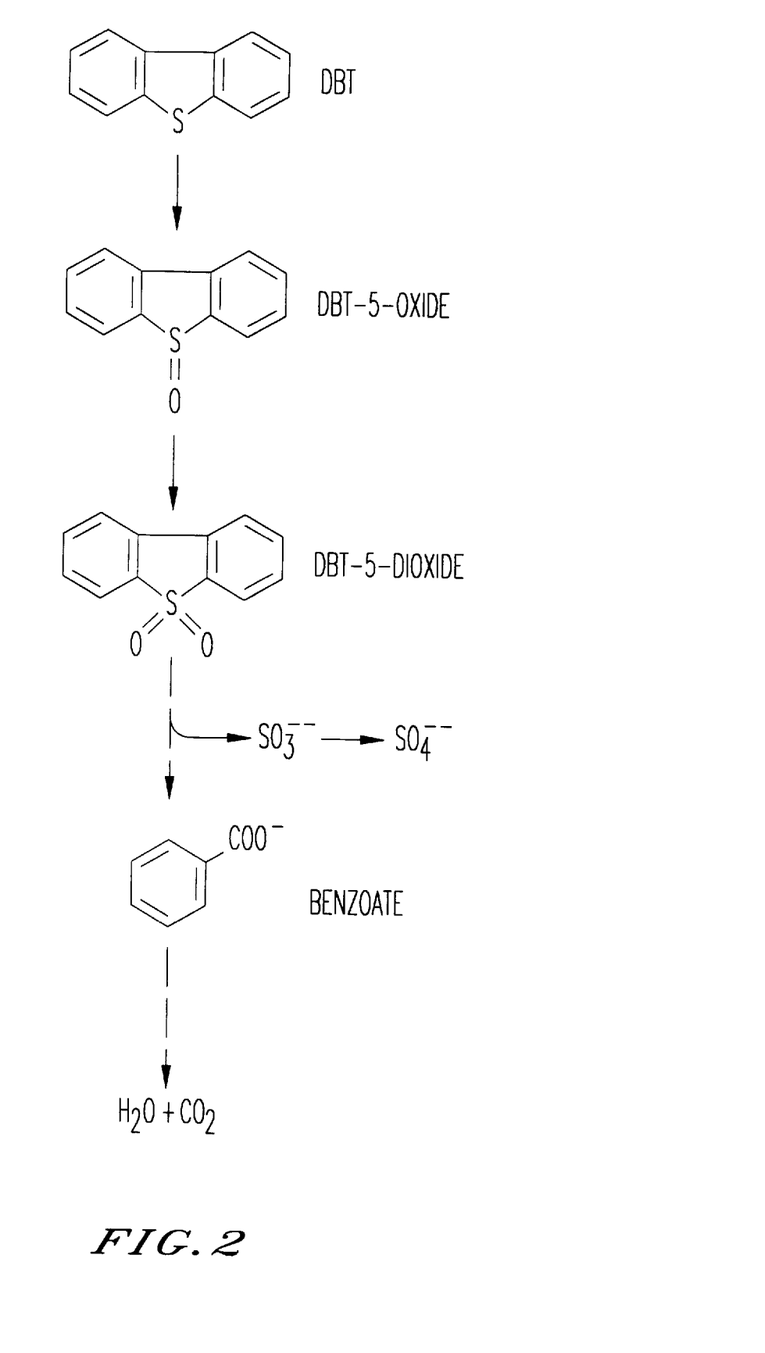
FIG. 2: Degradative pathway of dibenzothiophene proposed for Brevibacterium sp.

A strain of Brevibacterium sp. DO has also been described in literature (Van Afferden et al. Arch. Microbiol., 153: 324–328, 1990), capable of following the "4S" pathway through the first three passages, to reach the consequent complete mineralization of the DBT with a further metabolic step which leads to the production of benzoate according to the diagram shown in FIG. 2.

Grossman et al. have recently described a biological desulfuration process which is based on the use of strains of Arthrobacter capable of removing sulfur from DBT and 4,6-diethyldibenzothiophene (CA 2097217; Appl. and Envirom. Microbiol., 61: 4362–4366, 1995).

Even this process however has its disadvantages. In fact, the desulfurating activity of these strains is inhibited by low concentrations (1 mM) of the sulfate ion.

It has now been found that it is possible to overcome the drawbacks of the known art discussed above by means of a new strain of Arthrobacter capable of selectively opening the C-S bond of sulfurated organic molecules present in a carbonaceous material without degrading the carbonaceous structure of the molecule itself, without surfactants. This enables water consumption to be reduced with the use of simple equipment to separate the phases leaving the biological reactor. In addition, the desulfurating activity of the strain of the present invention is not influenced by concentrations equal to 46 mM of sulfate ion.

Samples of this strain were deposited on Feb. 9, 1996, at the Centraalbureau voor Schimmelcultures (CBS) where they received the filing number CBS 208.96.

DETAILED DESCRIPTION OF THE INVENTION

In order to isolate a microbic strain capable of degrading DBT by means of the "4S" pathway, soil taken from a bioremediation pilot plant of a site contaminated by crude oil with a high sulfur content, was used.

The isolation was carried out by successive enrichment and purification phases in a medium containing a carbon source and DBT as the only sulfur source. The results obtained showed the presence of strains capable of using the DBT. The subsequent isolation of microorganisms in a pure medium, recultured individually on a medium containing DBT as the only sulfur source, allowed a single strain to be selected capable of using the DBT as sulfur source. This strain was preliminarily marked with the abbreviation DS7.

In order to demonstrate that the DBT was not also used as carbon source, the DS7 strain was cultured in two mediums DS3 and DS4 containing in one case DBT as carbon source alone and in the other as carbon and sulfur source. The absence of growth in these mediums led to the assumption that the only use of DBT on the part of the strain was degradation via "4S".

Figure 3:
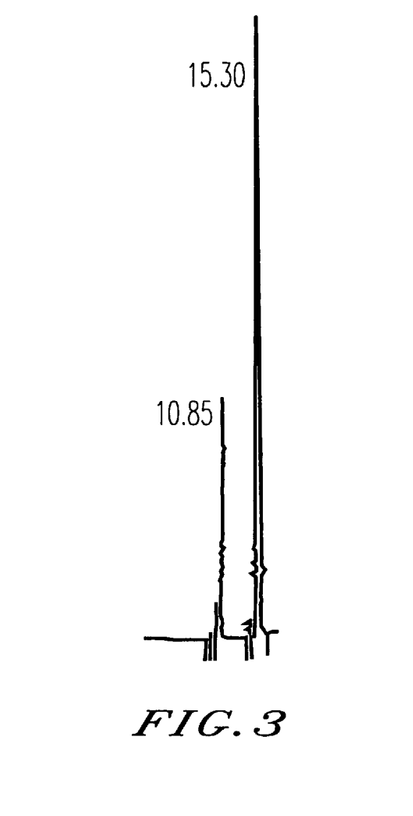
FIG. 3: Analysis of the extract from "resting cells" at the start of the reaction, via HPLC. The peaks correspond to 2-hydroxybiphenyl (RT=10.85), DBT (RT=15.30)
Figure 4:
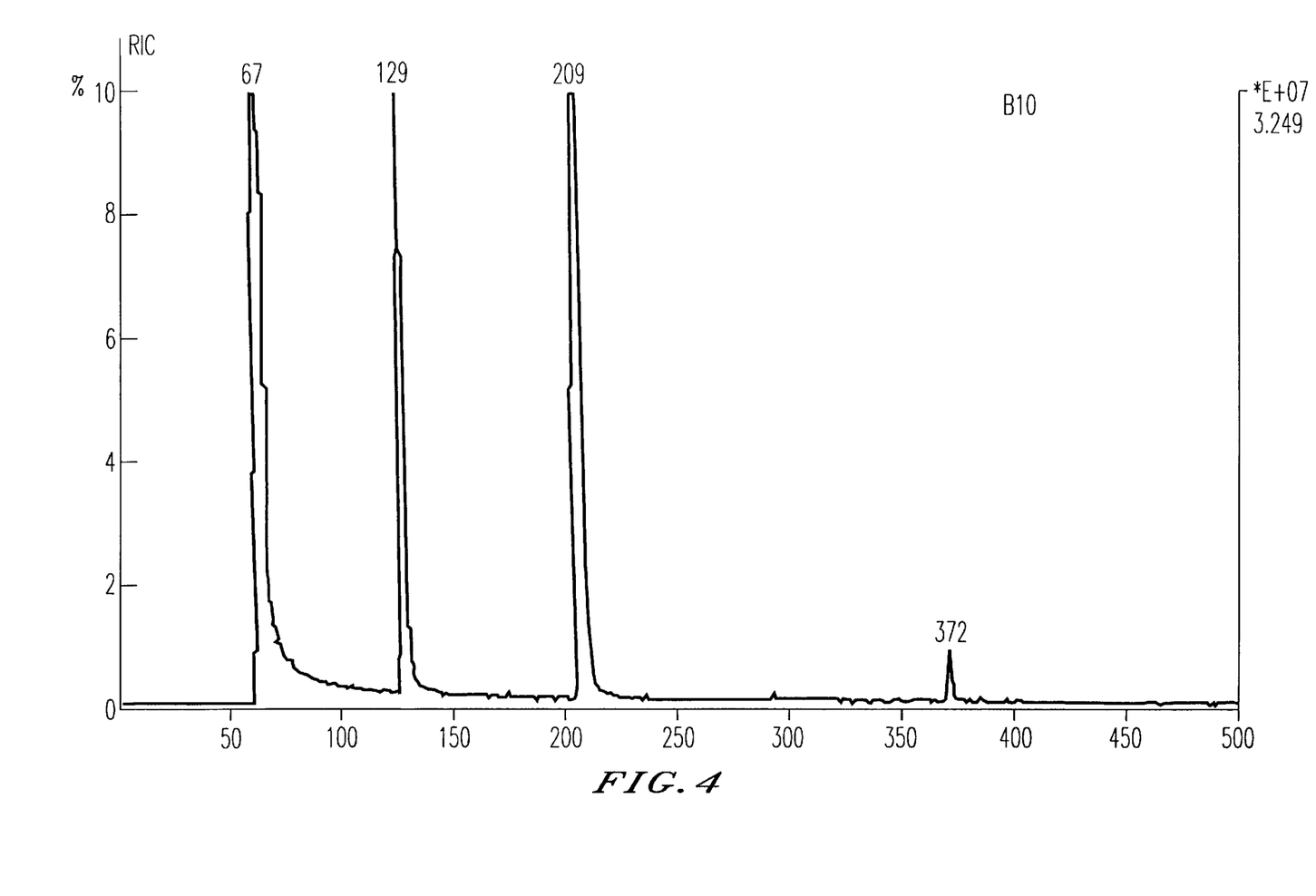
FIG. 4: Analysis of the extract from "resting cells" via GC-MS. The peaks correspond to the retention times 67 Ethyl Acetate; 129 2-hydroxybiphenyl; 209 DBT; 372 DBT oxide, respectively.

To confirm this hypothesis, the strain was cultured on DS2 medium (DBT as only sulfur source) and the biomass was used in "resting-cells" on DBT. The reaction products were extracted with ethyl acetate and analyzed via HPLC and GC/MS. The analyses confirmed the presence of intermediates and end-degradation product (2-hydroxybiphenyl) of DBT in accordance with the "4S" pathway (FIG. 3 and 4).

Figure 5:
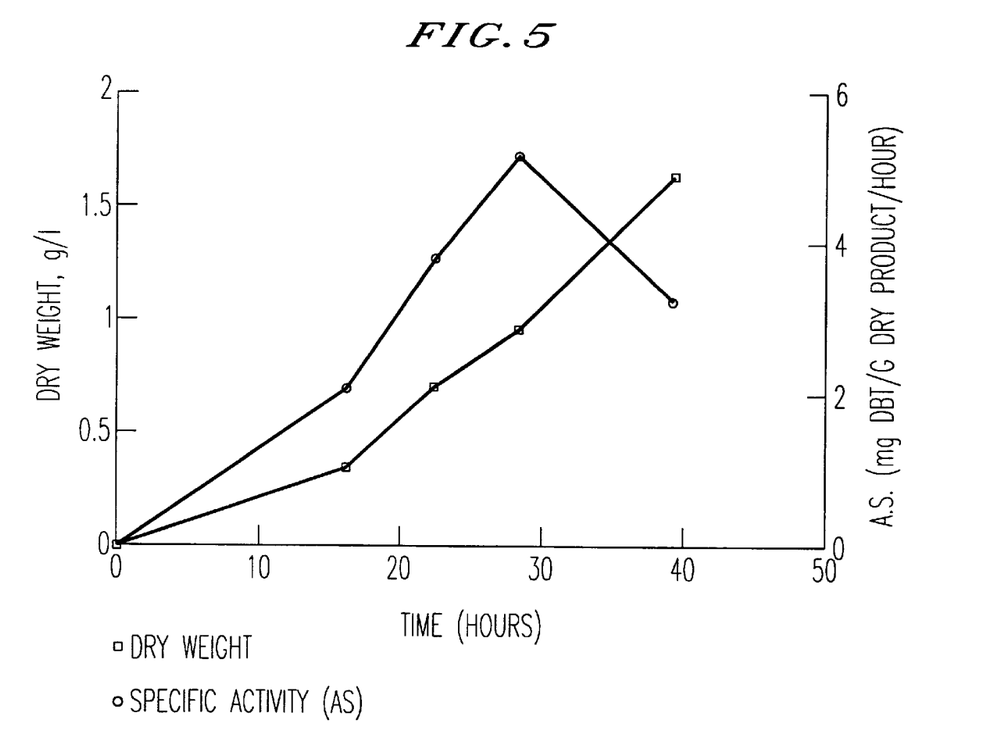
FIG. 5: Production kinetics of the enzymatic complex.

The production kinetics of the enzymes to be involved into desulfuration, in the various growth phases, was carried out by culturing the DS7 strain in a culture medium containing a carbon source and DBT as the only sulfur source (FIG. 5). The results obtained showed the following:
- the bacterium expresses its maximum enzymatic activity after over halfway of the exponential growth phase (28 hours);
- the stability of the enzymatic system is good as the activity is maintained even after long periods of conservation of the biomass (7 days at 4° C.);
- the strain DS7 expresses its activity on the main groups of sulfurated molecules present in straight-run gas oils, gas oils from hydrodesulfuration and the main streams coming from the atmospheric distillation of petroleum (cuts: 70°–160° C. 160°–230° C. and 230°–350° C.);
- the strain DS7 is capable of producing such emulsifying agents that, without the addition of external agents, good microemulsions/microdispersions can be formed;
- the phase forming microemulsions/microdispersions can be easily separated.

For the characterization of the strain DS7 reference was made to the procedures described in Bergey's Manual of Systematic Bacteriology (Volumes 1–4), Ed. 1989, Williams & Wilkins, Baltimore.

| MORPHOLOGICAL AND TINCTURIAL CHARACTERISTICS | |
|---|---|
| Gram-reaction | + (variable after 24 h) |
| Morphotype | pleomorpho, with V cells |
| Dimensions | 0.6 × 1 µm (stationary phase) |
| Mobility | none |
| Endospore | " |
| Capsule | " |
| Ziehl-Neelsen | – (after 24 hours) |
| metachromatic granules | – |
| CULTURAL CHARACTERISTICS | |
| Colony on Nutrient Agar | Beige/pinkish, humid |
| Elevation | convex |
| Chromogenesis | No |
| Pigment (with acids) | No |
| Pigment (with alkalies) | No |
| Surface | Smooth, shiny |
| Border | whole |
| Dimensions (diameter) | 1.5 mm (after 24 h) |
| Emulsionability | Rapid, in water |
| Colour change in Y.E. broth | Alkaline |
| PHYSIOLOGICAL CHARACTERISTICS | |
| β-galactosidase | + |
| Cytochrome-oxidase | – |
| Catalase | + |
| Urease | + |
| Gelatinase | – |
| Arginine dehydrolase | – |
| Lysine decarboxylase | – |
| Tryptophan deaminase | – |
| Nitrate→Nitrite reduction | – |
| Nitrate→N$_2$ reduction | – |
| Tolerance 330 mM NaCl | + |
| USES OF CARBON SOURCES | |
| Glycerol | + (oxidation) |
| D-Glucose | – |
| D-Fructose | – |
| D-Mannose | + (weak oxidation) |
| Galactose | + (weak oxidation) |
| L-Sorbose | – |
| Rhamnose | – |
| Dulcitol | – |
| Inositol | + (weak oxidation) |
| Mannitol | + (weak oxidation) |
| Sorbitol | + (weak oxidation) |
| Erythritol | – |
| D-Arabinose | – |
| L-Arabinose | – |
| Ribose | + (weak oxidation) |
| D-Xylose | – |
| L-Xylose | – |
| Adonitol | – |
| Arbutin | – |
| Esculin | + (hydrolysis) |
| Salicin | – |
| Cellobiose | – |
| Maltose | – |
| Lactose | + (weak oxidation) |
| Melibiose | – |
| Sucrose | – |
| Trealose | – |
| Inulin | – |
| Melezitose | – |
| D-Raffinose | – |
| Soluble starch | – |
| Glycogen | – |
| Xylitol | – |
| Gentibiose | – |
| D-Turanose | – |
| D-Lysose | – |
| D-Tagatose | – |
| D-Fucose | – |

-continued

| | |
|---|---|
| D-Arabitol | + (weak oxidation) |
| L-Arabitol | – |
| Amigdalin | – |
| β-Methyl-Xyloside | – |
| Malate | – |
| Acetate | – |
| Benzoate | – |
| Citrate | – |
| Gluconate | + (weak oxidation) |
| α-Methyl-D-Glucoside | – |
| α-Methyl-D-Mannoside | – |
| N-Acetyl-Glucosamine | – |

On the basis of the results of the morphological and cultural exams, it can be stated that the strain DS7 of the present invention cannot belong to the Mycobacterium, Nocardia, Nocardioides, Oerskovia and Arachnia species. In fact, unlike these species, DS7 does not have rigorous nutritional demands, it develops in short periods of time, it does not produce filaments (hyphae, aerial mycelium) on agarized nutritional medium, it is not resistent to treatment with acid according to Ziehl-Neelsen.

The strain DS7 has non-equivocal oxidative metabolic capacities and lacks the versatility of the facoltative respiratory strains belonging to the Corynebacterium genus or the capacity to grow in anaerobiosis typical of the Arachnia genus.

In addition, owing to its physiological characteristics and its distinctive behaviour with respect to the carbon sources to be used, it can be excluded that it belongs to the Rhodococcus genus. The strains belonging to this genus, in fact, have the capacity to use a wide range of carbon compounds and do not have β-galactosidase. In particular R.rhodochrous produces acid from Fructose, Glucose, Mannose, Sucrose, Mannitol, Trealose and does not grow on Lactose. The exclusion of its belonging to the Rhodococcus genus was also supported by comparative analysis of the membrane lipids. The tinctural and limited enzymatic characteristics distinguish it from the *Brevibacterium linens* strain which has the capacity of liquefying gelatine, produces an "almost cellular capsule" which is non-washable and an orange pigment if subjected to treatment with alkalies or acids.

The non-demanding behaviour of the strain DS7 with respect to the growth factors (it does not require supplements of vitamins or other principles), the "canonical" morphogenetic cycle (bacillary-ellipsoid with V cells in fresh cultures, coccoid with aging), the reactions with oxygen (it is an aerobe), its way of using carbon sources (only oxidative), the precise expression of some enzymatic activities (gelatinase, β-galactosidase), the tinctural characteristics (Gram-variable, Ziehl-Neelsen-negative, no capsule or endospore), would seem to direct the strain under examination towards the Arthrobacter genus.

The non-growth of the isolated strain on acetate and benzoate suggests that, although belonging to the same type, it is a different species to the Arthrobacter strain described by Grossman et al.

The desulfuration process by means of the Arthrobacter sp. strain of the present invention consists in putting this strain or the enzymatic complex isolated from this strain in contact with an emulsion or suspension of the substrate to be desulfurated in an aqueous medium (o viceversa). The emulsion or suspension is obtained, without surfactants, in equipment having mechanical systems or in mixers without parts in movement, such as for example mixers based on ejector systems. The mixing is carried out at room temperature and atmospheric pressure, with a volumetric ratio substrate to be desulfurated/aqueous phase of between 1:1 and 7:1, preferably 3:1. In this way it is possible to obtain a microemulsion or microsuspension which is stable with respect to the residence times in the oxidation reactor, times which generally vary depending on the type of petroleum fraction and relative sulfur content.

The desulfuration process of the present invention can be carried out on crude oils, on fractions which have undergone thermal treatment of atmospheric distillation under vacuum (fuel oils) and on gas oils coming from HDS plants to be subjected to forced desulfuration.

The desulfuration process of the present invention can be carried out batchwise or in continuous, preferably in continuous, and is characterized by the main operating phases listed hereunder:

(1) Culture of the bacterium DS7

The biological catalyst (biocatalyst) consisting of the bacterium DS7 or its enzymatic derivatives is prepared by culturing the cells in any type of fermenter, preferably continuous. The aqueous culture medium contains assimilable carbon sources, nitrogen sources, as well as various cations and anions.

Glycerinous water obtained as by-product from the soap-manufacturing industry can be used for example as low-cost carbon source. Nitrogen sources which can be used in the process of the present invention can be selected, for example, from ammonium salts such as ammonium nitrates, ammonium chloride or ammonium carbonate or urea.

The following cations and anions are equally suitable for the purposes of the present invention: potassium, sodium, magnesium, iron, calcium, acid phosphates and chlorides.

The culture medium additionally contains sulfur sources capable of inducing and maintaining the synthesis of the enzymatic complex having desulfurating activity and which can be selected from DBT, petroleum or its derivatives with a high content of sulfurated organic molecules. The aqueous phase necessary for the preparation of the culture medium can come from the subsequent step (4).

The growth of the cells is carried out at temperatures of between 20° and 35° C., preferably 30° C., under stirring and aeration (0.5–1 volume of air/volume of reactor per minute). The pH is maintained more or less at neutrality.

2. Preparation of the biocatalyst

The cultured cells are collected and separated from the culture medium with the typical procedure and equipment of the biotechnological industry. According to this processing they are concentrated in a stream which is such as to be fed to the subsequent biodesulfuration reaction.

Alternatively the cells can be subjected to separation processes of enzymatic extracts with a higher catalytic activity. These operations can also be carried out according to the normal biotechnological techniques (cell breakage, separation of the nucleic acids, etc.).

3. Biodesulfuration reaction

The reaction can be carried out in continuous or batch reactors. Continuous reactors are preferred either of the plug flow or stirred type (Continuous Stirred Tank Reactor, CSTR). The latter can be arranged in mono or multistep configurations.

The CSTR multistep configuration is the most suitable. In plug flow reactors, the suspension of the substrate to be desulfurated is fed into the aqueous medium previously formed.

In CSTR reactors the preparation of the emulsion can take place in the same reactors. They are therefore so produced as to put the biocatalyst in close contact with the oil phase to be desulfurated and the gaseous phase (air, enriched air, etc.) from which the oxygen necessary for the biological oxidation process of the sulfur is obtained.

Considering the strictly oleophilous nature of the strain DS7, the reaction can take place without surfactants using reduced quantities of water. A volumetric ratio material to be desulfurated/water of between 1:1 and 7:1, preferably 3:1, is conveniently used.

The oil phase and the aqueous phase can be fed in counter-current thus producing systems assimilable to liquid-liquid extractors with associated biological reaction. In these systems, in which each step consists of a mixer and a separator, the fresh catalyst can be produced using the water coming from the removal of the sulfates (see point 5). In this way it carries out its desulfurating activity with the greatest efficiency.

The desulfuration reaction is carried out at a temperature of between 20° and 40° C., preferably between 25° and 35° C., and at a pH of between 5 and 9, preferably between 6.5 and 7.5.

4. Separation of the phases at the outlet of the reactor

The use of phase separators capable of giving modest increases in the gravitational field (centrifuges with a limited number of revs, hydrocyclones etc.) is sufficient for the separation.

The following three streams are obtained from the separation:

a) The oil desulfurated phase which, after dehydration, can be sent for use. The dehydration operation is not problematical as the water is mainly associated with the biocatalyst whose removal is not difficult.

b) An aqueous phase containing small quantities of biocatalyst which can be eliminated with the usual techniques (centrifugation, filtration, etc..) The remaining aqueous stream is subjected to a removal step of the sulfates as described in point (5) and then recycled to step (1).

c) A mucilaginous phase mainly consisting of the biocatalyst together with oil and water. This stream, depending on the content of sulfates, can be recycled directly to the desulfuration reactor or subjected to removal of the sulfates which is carried out by resuspending the mucilaginous stream in water and subjecting the mixture to centrifugation. The residual aqueous stream is joined to that described in point b.

(5) Removal of the sulfates

The aqueous sources coming from step (4) are joined and biologically subjected to the removal of the sulfates with the use of sulfate-reducer anaerobic bacteria. This treatment can be carried out in conventional anaerobic reactors of the anaerobic filter type (operating with the biomass adsorbed on solid carriers) or of the Up-flow Anaerobic Sludge Blanket type (UASB, operating with aggregated biomass).

In this step the sulfates are reduced to soluble sulfides. Possible traces of hydrogen sulfide can be removed in the normal plants used in the petroleum industry, whereas the soluble sulfides can be reoxidated to elemental sulfur in a subsequent biological step using aerophilous or microaerophilous microbic biomasses such as for example the genus: Thiobacillus, Beggiatoa, Thiotrix, Thioploca, Paracoccus, etc.

Reactors functioning with adsorbed or aggregated biomass can also be used for the oxidation reaction of the sulfides to sulfur. The limited supplies of oxygen required make it preferable however in the case of microaerophilous microorganisms to use reactors in which the biomass is adsorbed on rotating carriers (Rotary Biological Contactor, RBC), whereas in the case of aerophilous microorganisms, configurations developed in height with a settler at the head, can be used.

The mesophilous nature of the microorganisms cited above makes it preferable for them to be used at temperatures close to room temperature, preferably regulated at about 30°–35° C. The preferred operating pH is close to neutrality, but acid values can be reached; the operating pressure corresponds to atmospheric pressure.

The sulfur leaving the reactors can be separated from the aqueous phase and from the biomass by means of sedimentation, washing and filtration of solids operations, melting of the sulfur and its separation. The melting of the sulfur takes place at 130° C. and enables a product to be obtained with such purities as to be sold on the market for the production of sulfuric acid.

The succession of operations for the removal of sulfur produces water with such contents of sulfates that, after integration with nutrients, it can be partly recycled to step (1) for the culture of the bacterium DS7 and partly reused for the resuspension of the biomass. With these operations depurative levels of the aqueous flushing streams are also obtained which are such as to enable the discharge into surface hydric systems either directly or after bland conventional aerobic post-treatment. This latter operation can be carried out in the water treatment plants normally available in the petroleum industry.

The following examples, which have the sole purpose of providing a better illustration of the present invention, should in no way be considered as limiting the scope thereof.

EXAMPLE 1
Isolation of Arthrobacter sp.

In order to isolate a microbic strain capable of degrading DBT via the "4S" pathway, soil was used, taken from a bioremediation pilot plant of a site contaminated (about 1.6% w/w) with a Sowedi crude oil containing a content of organic sulfur equal to about 6%.

100 g of soil were added to 200 ml of water and, after vigorous stirring and subsequent sedimentation, two 5 ml aliquots of surnatant were removed.

These aliquots were used to inoculate two 250 ml flasks each containing 50 ml of two different mediums (DS1 and DS2) whose composition, in bidistilled water, is shown in Table 1.

TABLE 1

| COMPONENTS | DS1 | DS2 |
|---|---|---|
| $KH_2PO_4$ | 10.0 g/l | 10.0 g/l |
| $NH_4Cl$ | 2.0 g/l | 2.0 g/l |
| $MgCl_2.6H_2O$ | 0.2 g/l | 0.2 g/l |
| DBT | — | 0.5 g/l |
| Succinic acid | 4.0 g/l | 4.0 g/l |
| $FeCl_3$ | 10.0 mg/l | 10.0 mg/l |
| $CaCl_2$ | 20.0 mg/l | 20.0 mg/l |
| pH (with NaOH) | 6.4 | 6.4 |

The two flasks were placed in an orbital NBS incubator at 30° C., at 200 rpm. 5 successive sub-cultures were carried out on the same mediums at intervals of 72 hours using inocula equal to 5% volume/volume.

The DS1 medium served as control to show the basic growth due to the sulfur impurities present in the other nutrients. The growth on DS2 was significantly higher justifying the hypothesis of the use of the sulfur of the DBT on the part of microorganisms present in the medium.

The culture broth obtained after 5 sub-cultures on DS2 was used to inoculate (at various dilutions) Petri plates containing a maximum agarized medium (Nutrient Agar®, DIFCO) and left to incubate for 48 hours at 30° C. Among all the colonies developed 7 were selected apparently different from each other in their morphological and/or pigmentation characteristics.

The seven strains were first isolated in single Petri plates on Nutrient Agar® as described above, then inoculated into flasks containing DS2 medium to test their capacity to use DBT as sulfur source. Only one strain proved to be capable of growing under these conditions.

EXAMPLE 2
Verification of the degradative pathway

A) The only strain capable of growing on DBT as sulfur source (called DS7) was used as inoculum for the culture mediums DS3 and DS4 having the compositions indicated in table 2.

TABLE 2

| COMPONENTS | DS3 | DS4 |
|---|---|---|
| $KH_2PO_4$ | 10.0 g/l | 10.0 g/l |
| $NH_4Cl$ | 2.0 g/l | 2.0 g/l |
| $MgCl_2.6H_2O$ | — | 0.2 g/l |
| $MgSO_4.7H_2O$ | 0.2 g/l | 0.5 g/l |
| DBT | 0.5 g/l | 0.5 g/l |
| Succinic acid | — | — |
| $FeCl_3$ | 10.0 mg/l | 10.0 mg/l |
| $CaCl_2$ | 20.0 mg/l | 20.0 mg/l |
| pH (with NaOH) | 7.2 | 7.2 |

In these mediums the DBT was supplied both as sole carbon source (DS3, sulfur supplied as sulfate) and sulfur and carbon source (DS4).

The non-growth on these mediums was interpreted as an expression of the desulfurating activity of DS7.

B) Testing of the presence of intermediates and the end product (2HBP) according to the "4S" pathway The strain DS7 was cultured on DS2 medium for 28 hours at 30° C.; the culture broth collected was centrifuged and washed twice with phosphate buffer 10 g/l at pH 7.2.

The biomass, equivalent to about 100 mg of dry substance, was suspended in 25 ml of the same phosphate buffer and put in a flask. 0.625 ml of a solution of dibenzothiophene 40 mM in ethanol were added to the flask, under stirring. The initial concentration of the dibenzothiophene in the reaction medium was therefore equal to 1 mM. 2 ml portions of the mixture obtained were placed in hermetically closed ampules and pressurized with oxygen at 2 bars. After preset incubation periods, 2 ml of ethyl acetate were added to the ampules to carry out the extraction of the DBT and its derivatives. The extracts obtained were analyzed via HPLC (FIG. 3) and GC/MS (FIG. 4).

Figure 3A:
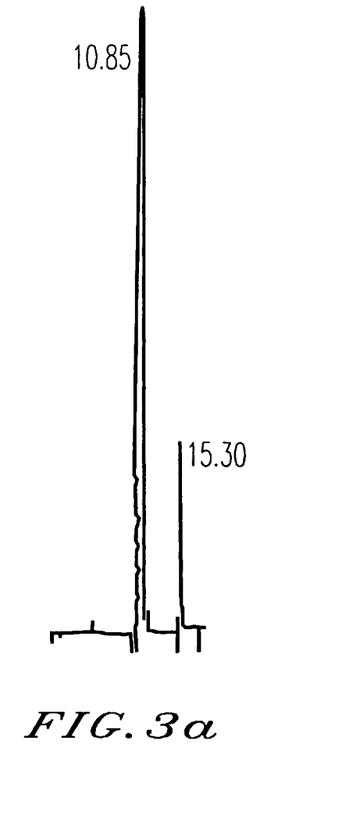
FIG. 3a: Analysis of the extract from "resting cells" via HPLC after 2 hours of reaction under optimum conditions. The DBT present at the beginning of the reaction has been transformed into 2-HBP.
Figure 3B:
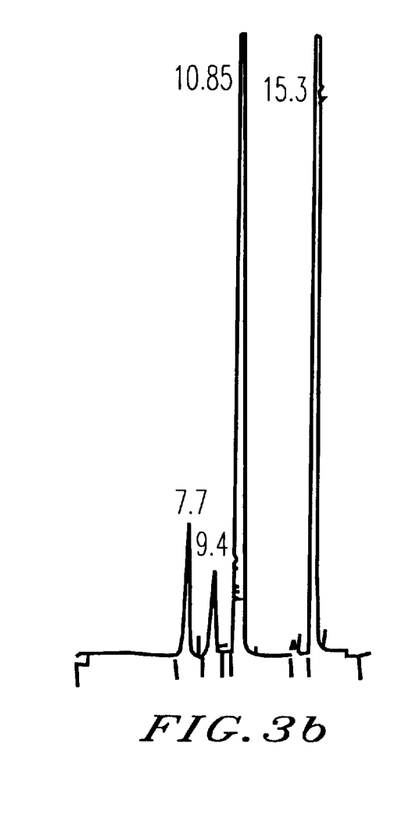
FIG. 3b: HPLC analysis carried out on a sample of cells conserved for 7 days at 4° C. From this analysis the "4-S" pathway is confirmed; DBT-SO (7.7); DBT-sulfone (9.4).

The results indicated in FIGS. 3 and 3a show that the DBT is almost entirely converted to 2-hydroxy-biphenyl after two hours of reaction. It should be noted that the 2-hydroxybiphenyl verified in FIG. 3 may be due to the immediate transformation of DBT to 2-HBP and to the 2-HBP bioabsorbed by the microorganism in the fermentation phase. The presence of all the degradation products of DBT in accordance with the "4S" pathway can be verified in FIG. 3b. These products can be seen only with cells having a reduced catalytic activity, as occurs after their conservation at 4° C. for 7 days or with kinetics run with oxygen limitation.

EXAMPLE 3
A) Kinetics of the enzymes production

To verify the production trend of the enzymes involved in the desulfuration in the various growth phases, a 2 litre flask containing 500 ml of the DS2 medium modified in order to have a lower concentration of inducer (from 0.5 g of DBT/l to 20 mg of DBT/l) was inoculated with the strain DS7. The inoculum equal to 25 ml was obtained from a previous culture on the same medium carried out in an Erlenmeyer flask. The flask was incubated under the same conditions described above.

Aliquots of culture broth were taken at the 16th, 22nd, 28th and 39th hour. The following parameters were determined on the samples: Optical density at 660 nm, dry weight and specific desulfurating activity. The dry weight was determined as fixed residue at 105° C., after washing of the biomass with bidistilled water. The specific activity was determined on aliquots of culture broth equal to 20 ml. These were centrifuged at 8000 gravities for 10 minutes, resuspended in Tris-HCl buffer 20 mM at pH 7.2 and centrifuged again. The biomass was resuspended in the same buffer so as to have a final volume of 9.75 ml. The cellular suspension obtained was transferred to a 50 ml flask to which 0.25 ml of DBT 40 mM in ethanol were added. The flask was incubated at 30° C. under stirring and, at preset times, aliquots of the mixture were taken and analyzed via HPLC. The results obtained are shown in FIG. 5. From this figure it can be seen how the maximum expression of the enzymatic activity is recorded when the bacterium is situated over halfway of its exponential growth phase.

B) Induction of the enzymatic activity by means of petroleum fractions

For this purpose the strain DS7 was cultured on DS2 medium in which the dibenzothiophene was substituted in its functions as inducer and sulfur source by:
(a) 0.5 ml/l of petroleum fraction 230°–350° C. containing 13600 ppm of sulfur, (b) 1 ml/l of gas oil from HDS with 2000 ppm of sulfur. The cultures were carried out in 500 ml flasks according to the procedure described in point A. After 44 hours the biomass contained in 20 ml of culture broth was subjected to analysis to determine the specific activity. This parameter for sample (a) proved to be equal to 4.3 mg of dry DBT/g/hour, whereas for sample (b) it had the value of 2.6 mg of dry DBT/hour. These results indicate that the petroleum products examined are such as to induce the synthesis of the enzymatic complex.

EXAMPLE 4
Desulfuration test of gas oil

A gas oil was used which had undergone standard HDS desulfuration treatment with a residual sulfur content of about 2000 ppm and 47 ppm of fluidifying additive DODIFLOW®V 3905-2. A non-desulfurated gas oil containing 10200 ppm of sulfur was contemporaneously experimented. The biomass obtained after culture in continuous (dilution rate 0.09 $h^{-1}$, culture medium analogous to that of example 2A) was separated by centrifugation and washed twice with Tris-HCl buffer at pH 7.2. It was then resuspended in the same buffer so as to have a concentration of dry product equal to 38 mg/ml.

7.5 ml of cellular suspension and 2.5 ml of gas oil were then placed in 53 ml bowls. The bowls were put at a pressure of 2.0 bars with oxygen and incubated at 30° C. under stirring at 200 rpm (standard tests). To verify any possible side reactions under the reaction conditions (aqueous and oxidating environment), a test was carried out as reference, in which the cellular suspension was substituted with Tris-HCl buffer. A third test was also carried out in the presence of petroleum fractions and cells taken as zero time. The standard and reference tests were interrupted after 24 hours. The reaction mixture was subjected to centrifugation (8000 gravities for 20 minutes). The oil phase recovered was analyzed via gas chromatography using a Hewlett-Packard instrument (Mod.5890), equipped with an atomic emission detector (Atomic Emission Detector®, AED, Mod. HP 5921-A). The chromatographic separations were carried out with a capillary column of the type DB-1 of J.W.S. The results, after subtraction of the zero time contributions, are shown in table 3. It should be noted that the reference test did not show any collateral phenomena.

TABLE 3

| Gas oil | Sulfur, ppm | Desulfuration % |
|---|---|---|
| Straight-run | 10,200 | 13.5 |
| From HDS | 2,000 | 19.7 |

From this table it can be seen the the bacterium DS7 conducts its activity on both the gas oils tested.

In addition, as can be observed from the data indicated in table 4, the strain DS7 is active on the main groups of sulfurated molecules contained in the gas oils tested.

TABLE 4

| | Desulfuration % (24 hours) | |
|---|---|---|
| Molecules | Straight-run | From HDS |
| C3-BT | 10.2 | 18.9 |
| DBT | 10.3 | 16.8 |
| C1-DBT | 10.3 | 22.9 |
| C2-DBT | 7.1 | 5.1 |

EXAMPLE 5
Desulfuration in the presence and absence of emulsifying agents

The tests were carried out using a model system consisting of dodecane containing dibenzothiophene at concentrations of 0.3 and 3%.

Operating with DBT at 0.3 three different tests were carried out to verify the influence of an emulsifying agent on the desulfurating activity of the strain DS7. The first without the addition of an emulsifying agent, the second and third respectively contained 0.25 and 0.5% of Triton N-101.

For all the tests the following procedure was adopted: aliquots (2.5 ml) of the oil phase were put in 8 bowls (2 per test) with a capacity of 53 ml. 7.5 ml of a buffer Tris-HCl solution 20 mM at pH 7.2 containing the cells in a ratio of 12.5 mg of dry product/ml (about 100 mg of total dry product per bowl), were then added to each bowl. The bowls were closed and brought to 2 bars with oxygen. of the eight bowls, four, which represent zero time, immediately after the addition of the oxygen were placed in an ice bath and immediately analyzed as described below. The other four were incubated under stirring (200 rpm), in a bath thermostat-regulated at 30° C. for 16 hours.

The reaction mixtures contained in the eight bowls were transferred to glass test-tubes and centrifuged at 8000 gravities for 15 minutes. Aliquots of dodecane were suitably diluted with ethyl acetate and analyzed via HPLC. The results obtained, after subtraction of the zero time, are shown in table 5.

TABLE 5

| Emulsifying agent (Triton N-101) | DBT % | Desulfuration % |
|---|---|---|
| — | 0.3 | 35.1 |

TABLE 5-continued

| Emulsifying agent (Triton N-101) | DBT % | Desulfuration % |
|---|---|---|
| 0.25 | 0.3 | 14.6 |
| 0.5 | 0.3 | 16.4 |
| — | 3 | 3.1 |

The above results indicated that the bacterium DS7 does not require commercial emulsifying agents to be able to effect its desulfurating activity. On the contrary it should be noted that external emulsifying agents have a considerable inhibiting effect.

EXAMPLE 6

Desulfuration test in model systems.

The tests were carried out to show that the oleoficity of the strain DS7 reduces the water consumption of the process.

For this purpose, using a solution of DBT at 0.3% in dodecane and a quantity of biomass in each test, three distinct tests were carried out. In the first 2 ml of cellular suspension (19.8 mg of dry product/ml of water) and 4 ml of dodecane (oil phase:aqueous phase ratio 2:1), were used. The second was prepared in the same way increasing however the volume of dodecane+DBT (ratio 3:1) to 6 ml. The two tests were compared with a third in which the ratio oil phase:aqueous phase was equal to 1:1.

The mixtures were reacted in 6 50 ml ampules (2×test). Oxygen was bubbled into the ampules to 1.5 bars, hermetically closed and incubated under stirring at 30° C. Three ampules at zero time, and another three at the 20th hour were depressurized. After the separation phases, an aliquot of organic phase was removed, ethyl acetate added (4 volumes/per volume) and HPLC analysis applied.

Table 6 shows the results obtained at the 20th hour after deduction of the zero time.

TABLE 6

| Ratio dodecane/ aqueous phase | Desulfuration mg degraded DBT/g dry product |
|---|---|
| 1:1 | 38.1 |
| 2:1 | 36.1 |
| 3:1 | 34 |

As can be observed from this table, the desulfuration takes place at similar levels also in the presence of smaller quantities of water.

EXAMPLE 7

Influence of the concentration of sulfates on the desulfurating activity of the strain DS7

The tests were carried out using three identical quantities of dry DS7 biomass (13 mg/ml) suspended:

- The first (blank) in a tris-HCl buffer 20 mM at pH 7.2
- The second in the same buffer containing 15.5 mM of $Na_2SO_4$ (equivalent to 500 ppm of sulfur).
- The third in the same buffer containing 46.5 mM of $Na_2SO_4$ (1500 ppm of S).

After adding the DBT (1 mM) the three tests were carried out at 30° C., in a stirred bath at 200 rpm. After 2 and 4 hours the residual concentration of DBT was determined. Table 7 shows the results obtained.

TABLE 7

| Sulfates | Desulfuration (%) | |
|---|---|---|
| mM | 2 h | 4 h |
| 0 | 75 | 100 |
| 15.5 | 55 | 100 |
| 46.5 | 50 | 100 |

EXAMPLE 8

Desulfuration tests of petroleum fractions

The following fractions were used coming from the atmospheric distillation of a crude oil with a total sulfur content of 1.36% (Belaym crude oil): 1) fraction 70°–160° C., 2) fraction 160°–230° C., 3) fraction 230°–350° C. The sulfur content in each fraction was respectively equal to: 400, 2400 and 13600 ppm. A further quantity of sulfur equal to 160 ppm as dibenzothiophene was added to each fraction. This was to be able to have a precise reference compound.

Five ml of petroleum fraction were mixed with 5 ml of phosphate buffer 0.1M at pH 7. The cells were used at two different concentrations equal to 16 and 32 mg of dry product/ml of buffer, respectively. The ampules containing the reaction mixtures were brought to a pressure of 1,5 bars with oxygen and hermetically closed. Comparative samples were used consisting of the same mixtures in which the cells, before being put in contact with the oil phases, were deactivated by raising the temperature to 121° C. for 20 minutes.

The whole content of the single ampules was centrifuged (8000 gravities for 20 minutes) and analyzed via GC/AED according to what is described in example 4, at preset times (24 and 48 hours). The chromatographic separations were carried out with a capillary column of the type DB-1 of J.W.S. The total desulfuration levels obtained are shown in table 8.

TABLE 8

| | Cells | | | |
|---|---|---|---|---|
| | 16 mg/l Desulfuration % | | 32 mg/l Desulfuration % | |
| Fraction | 24 hr | 48 hr | 24 hr | 48 hr |
| 70–160° C. | | | 2.5 | 4.6 |
| 160–230° C. | 3.2 | 5.4 | 4.1 | 8.5 |
| 230–350° C. | 4.1 | 7.9 | 8.2 | 14.1 |
| Blank | — | — | — | — |

The desulfuration levels of the following main groups of compounds were also determined on the last fraction: Methyl-benzothiophene (C1-BT), Ethyl-benzo-thiophene (C2-BT), Propyl-benzothiophene (C3-BT) and Alchyl-dibenzothiophene (C1-C3-DBT). The results obtained are shown in Table 9.

TABLE 9

| | Cells | | | |
|---|---|---|---|---|
| | 16 mg/l Desulfuration % | | 32 mg/l Desulfuration % | |
| Molecules | 24 hr | 48 hr | 24 hr | 48 hr |
| C1-BT | 3.5 | 7.7 | 5.9 | 14.3 |

TABLE 9-continued

|  | Cells | | | |
|---|---|---|---|---|
|  | 16 mg/l Desulfuration % | | 32 mg/l Desulfuration % | |
| Molecules | 24 hr | 48 hr | 24 hr | 48 hr |
| C2-BT | 4.2 | 8.1 | 8.4 | 16.2 |
| C3-BT | 4.5 | 8.3 | 7.7 | 15.1 |
| C1-C3-DBT | 3.4 | 7.6 | 8.9 | 17.9 |

EXAMPLE 9

Separation tests of the water-oil emulsions and recovery of the catalyst.

100 ml of a homogeneous suspension of cells in phosphate buffer 0.1M at pH 7 (32 mg of dry product per ml) were put in contact with an equal volume of the same desulfurated gas oil used in example 4. The containers were closed, placed in an oxygen atmosphere at 2 bars and incubated at 30° C. under stirring at 200 rpm. A comparative test was carried out by adding Triton N-10 to the mixture in a ratio of 0.25% v/v. After 24 hours the mixtures were centrifuged at 2000, 4000 and 8000 gravities. The volumes of the different phases recovered are shown in Table 10.

TABLE 10

|  | with emuls. agent Phases obtained (ml) | | | without emuls. agent Phases obtained (ml) | | |
|---|---|---|---|---|---|---|
| Gravity | oil | aqueous | emulsion | oil | aqueous | emulsion |
| 2,000 | 76 | 2 | 122 | 83 | 38 | 79 |
| 4,000 | 81 | 3 | 116 | 89 | 41 | 70 |
| 8,000 | 83 | 6 | 111 | 91 | 48 | 61 |

In this Table it can be seen that in all cases the oil and aqueous phases recovered without the addition of an emulsifying agent are higher than those in which the emulsifying agent has been used. It should be noted in the latter case that the aqueous phase recovered is practically negligible.

With the use of the surfactant the separation of an aqueous phase to be recycled to the reactor, after removal of the sulfates would therefore seem to be extremely difficult.

The advantages deriving from the use of the strain DS7, which does not require the use of emulsifying agents, are evident. In fact with centrifugation at low gravity it is possible to separate:
- a limpid desulfurated oil phase;
- a limpid aqueous phase to be subjected to separation of the sulfates; and
- an emulsifying phase which contains all the active desulfurating cells which can be recycled to the oxidation reactor.

We claim:

1. A biologically pure culture of Arthrobacter sp. CBS 208.96 capable of selectively opening the C-S bond of sulfurated organic molecules present in a fossil fuel without destroying the carbonaceous structure.

2. A process for removing organic sulfur from a fossil fuel by the selective opening of the C-S bond of sulfurated organic molecules which comprises:

(a) putting an emulsion or suspension of said fossil fuel in contact with the microorganism Arthrobacter sp. CBS 208.96 or its enzymatic derivatives, at a pH of between 5 and 9 and at a temperature of between 20° and 40° C., in an oxidating atmosphere at a pressure varying from atmospheric pressure to 3 bars;

(b) separating from the reaction mixture obtained in (a) a desulfurated oil phase, an aqueous phase and a mucilage phase consisting of the biocatalyst Arthrobacter sp. CBS 208.96 associated with oil and water;

(c) recycling the mucilage phase to the desulfuration step (a);

(d) treating the aqueous phase with anaerobic and aerobic microorganisms capable of removing the sulfate transforming it into sulfur; and (e) recycling the water completely purified of sulfur to step (a).

3. The process according to claim 2, wherein in step (a) the emulsion of fossil fuel is obtained by mixing, without surfactants, with water using a volumetric ratio fossil fuel/water of between 1:1 and 7:1.

4. The process according to claim 3, wherein the volumetric ratio is 3:1.

5. The process according to claim 2, wherein in step (c) the mucilage phase is washed with water before being recycled to step (a) and the washing water is treated as described in steps (d) and (e).

6. The process according to claim 2, wherein in step (a) the pH is between 6.5 and 7.5.

7. The process according to claim 2, wherein in step (a) the temperature is between 25° and 35° C.

8. The process according to claim 2, wherein the fossil fuel is crude oil, petroleum fractions, petroleum distillates and residues of petroleum distillation.

9. The process according to claims 2 to 7, carried out in continuous.

* * * * *

UNITED STATES PATENT AND TRADEMARK OFFICE
CERTIFICATE OF CORRECTION

PATENT NO. : 5,874,295
DATED : February 23, 1999
INVENTOR(S) : Eugenio FASCETTI et al.

It is certified that error appears in the above-identified patent and that said Letters Patent is hereby corrected as shown below:

On the title page, item [30], the Foreign Application Priority Data should read:

--Mar. 12, 1996 [IT] Italy .........................................MI96A0477--

Signed and Sealed this

Seventh Day of September, 1999

Attest:

Q. TODD DICKINSON

Attesting Officer

Acting Commissioner of Patents and Trademarks